(12) United States Patent
Chen et al.

(10) Patent No.: US 7,547,764 B2
(45) Date of Patent: *Jun. 16, 2009

(54) ORFF AND ORFF' POLYPEPTIDES, NUCLEIC ACID MOLECULES ENCODING THE POLYPEPTIDES AND APPLICATIONS THEREOF

(75) Inventors: Jiann-Hwa Chen, Taichung (TW); Pei-Tseng Lee, Taichung (TW); Yin Liu, Taichung (TW)

(73) Assignee: National Chung Hsing University, Taichung (TW)

( * ) Notice: Subject to any disclaimer, the term of this patent is extended or adjusted under 35 U.S.C. 154(b) by 287 days.

This patent is subject to a terminal disclaimer.

(21) Appl. No.: 11/649,623

(22) Filed: Jan. 4, 2007

(65) Prior Publication Data

US 2008/0287660 A1 Nov. 20, 2008

Related U.S. Application Data

(62) Division of application No. 10/983,151, filed on Nov. 5, 2004, now Pat. No. 7,186,562, which is a division of application No. 10/232,459, filed on Aug. 30, 2002, now Pat. No. 6,887,980.

(60) Provisional application No. 60/316,546, filed on Aug. 31, 2001.

(51) Int. Cl.
*C07K 14/00* (2006.01)
(52) U.S. Cl. ...................................... 530/350
(58) Field of Classification Search ................ None
See application file for complete search history.

(56) References Cited

U.S. PATENT DOCUMENTS 5,776,889 A 7/1998 Wei et al.
6,887,980 B2 * 5/2005 Chen et al. .................. 530/350

OTHER PUBLICATIONS

Lazar, et al. *Mol. Cell. Biol.* vol. 8 (1988) pp. 1247-1252.

* cited by examiner

*Primary Examiner*—Karen Cochrane Carlson
(74) *Attorney, Agent, or Firm*—Ladas and Parry LLP

(57) ABSTRACT

The invention relates to novel pathogenic OrfF and OrfF' polypeptides derived from *Xanthomonas campestris* pv. *campstris*, the nucleic acid molecules encoding the polypeptides and the uses of the same for detecting or preventing a black-rot disease of a crucifer plant, making organic fertilizer or composting and being a biofilter for degradation of organic compounds.

4 Claims, 13 Drawing Sheets

TGGAGCCAGAATTCGACGCCAAATTCAGAAAACGAAGGCATGTACAACGTC
                                        M   Y   N   V
AGCGGAGGAACATTAAAATTAGGTGATCACCTAACTGCTAAGGACTCTTCCAT
 S   G   G   T   L   K   L   G   D   H   L   T   A   K   D   S   S   I
CTTCATATCGGCCGATAAGAAAAAGATCGAGTCCTACTCAATCTGGAAG
 F   I   S   A   D   K   K   K   I   E   S   V   L   N   L   E   G
GTTCCTGGGTTTCTCGTCAGGACTTCAAGATTCGATATCCGAATTATCTGATTT
 V   P   G   F   L   V   S   R   Q   D   F   K   I   R   Y   P   N   Y   L   I   S
CAAATATTCCGAGAGGACAGAGTTCAGAAACATTGACTCTGGCCGTTATT
 N   I   P   R   G   Q   S   S   S   E   T   L   T   L   A   V   I
AAAAATCAGGAGAAGATGGAGTTTTCGTTCCCAGAAACCTCCCCAGATTGCCT
 K   N   Q   E   K   M   E   F   S   F   P   E   T   S   P   D   C   L
AAGTGCCATTCGCATAGCGCCAGCAGACGCACAGATGCTTAAGCTGCGGAA
 S   A   I   R   I   A   P   A   D   A   Q   M   L   K   A   A   E
GCATTTAATTAATAAGGCATACTTGAAAT
 A   F   N   *

Fig. 1

1
ATGACAAACTTCCTTAACAGATCATCATATCCCTACTTTATAATAACACTCCTTGCTGCT
1        M  T  N  F  L  N  R  S  S  Y  P  Y  F  I  I  T  L
L  A  A

61
TTGATTGCACCTTCAGCATATGCAACTAAAATTTCAGCAGCGACAGCAGCGGATGCTGCT
21       L  I  A  P  S  A  Y  A  T  K  I  S  A  A  T  A  A
D  A  A

121
CGTGCGTTTGAACTAGCCGAAGAAATTTCGAGAAATCTCAAAAAATCACCCTCTGAATTT
41       R  A  F  E  L  A  E  E  I  S  R  N  L  K  K  S  P
S  E  F

181
ATTAATTCATGGCCTGGAGCCAGAATTTCGACGCCAAATTCAGAAAACGAAGGCATGTAC
61       I  N  S  W  P  G  A  R  I  S  T  P  N  S  E  N  E
G  M  Y

241
AACGTCAGCGGAGGAACATTAAAATTAGGTGATCACCTAACTGCTAAGGACTCTTCCATC
81       N  V  S  G  G  T  L  K  L  G  D  H  L  T  A  K  D
S  S  I

Fig. 11 A

```
301
TTCATATCGGCCGATAAGAAAAAGATCGAGTCAGTCCTACTCAATCTGGAAGGTTCCTGC
101         F   I   S   A   D   K   K   K   I   E   S   V   L   L   N   L   E
G   S   C

361
GTTTCTCGTCAGGACTTCAAGATTCGATATCCGAATTATCTGATTTCAAATATTCCGAGA
121         V   S   R   Q   D   F   K   I   R   Y   P   N   Y   L   I   S   N
I   P   R

421
GGACAGAGTAGTTCAGAAACATTGACTCTGGCCGTTATTAAAAATCAGGAGAAGATGGAG
141         G   Q   S   S   E   T   L   T   L   A   V   I   K   N   Q   E
K   M   E

481
TTTTCGTTCCCAGAAACCTCCCCAGATTGCCTAAGTGCCATTCGCATAGCGCCAGCAGAC
161         F   S   F   P   E   T   S   P   D   C   L   S   A   I   R   I   A
P   A   D

541         GCACAGATGCTTAAAGCTGCGGAAGCATTTAATTAA
181         A   Q   M   L   K   A   A   E   A   F   N
```

Fig. 11 B

A
B
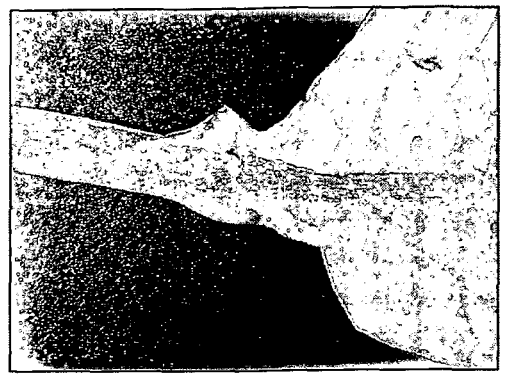
C
D
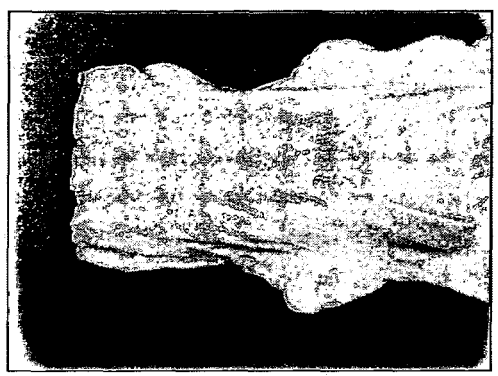
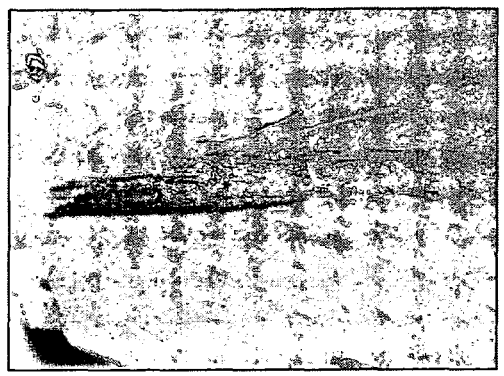
Fig. 12

SEQUENCE LISTING

<160> NUMBER OF SEQ ID NOS: 10

<210> SEQ ID NO 1
<211> LENGTH: 113
<212> TYPE: PRT
<213> ORGANISM: Xanthomonas campestris

<400> SEQUENCE: 1

Met Tyr Asn Val Ser Gly Gly Thr Leu Lys Leu Gly Asp His Leu Thr
1               5                   10                  15

Ala Lys Asp Ser Ser Ile Phe Ile Ser Ala Asp Lys Lys Lys Ile Glu
                20                  25                  30

Ser Val Leu Leu Asn Leu Glu Gly Ser Cys Val Ser Arg Gln Asp Phe
            35                  40                  45

Lys Ile Arg Tyr Pro Asn Tyr Leu Ile Ser Asn Ile Pro Arg Gly Gln
        50                  55                  60

Ser Ser Ser Glu Thr Leu Thr Leu Ala Val Ile Lys Asn Gln Glu Lys
65                  70                  75                  80

Met Glu Phe Ser Phe Pro Glu Thr Ser Pro Asp Cys Leu Ser Ala Ile
                85                  90                  95

Arg Ile Ala Pro Ala Asp Ala Gln Met Leu Lys Ala Ala Glu Ala Phe
                100                 105                 110

Asn

<210> SEQ ID NO 2
<211> LENGTH: 400
<212> TYPE: DNA
<213> ORGANISM: Xanthomonas campestris

<400> SEQUENCE: 2
tggagccaga atttcgacgc caaattcaga aaacgaaggc atgtacaacg tcagcggagg      60
aacattaaaa ttaggtgatc acctaactgc taaggactct tccatcttca tatcggccga     120
taagaaaaag atcgagtcag tcctactcaa tctggaaggt tcctgcgttt ctcgtcagga     180
cttcaagatt cgatatccga attatctgat ttcaaatatt ccgagaggac agagtagttc     240
agaaacattg actctggccg ttattaaaaa tcaggagaag atggagtttt cgttcccaga     300
aacctcccca gattgcctaa gtgccattcg catagcgcca gcagacgcac agatgcttaa     360
agctgcggaa gcatttaatt aataaggcat acttgaaaat                           400

<210> SEQ ID NO 3

-continued

<211> LENGTH: 191
<212> TYPE: PRT
<213> ORGANISM: Xanthomonas campestris

<400> SEQUENCE: 3

Met Thr Asn Phe Leu Asn Arg Ser Ser Tyr Pro Tyr Phe Ile Ile Thr
1 5 10 15

Leu Leu Ala Ala Leu Ile Ala Pro Ser Ala Tyr Ala Thr Lys Ile Ser
20 25 30

Ala Ala Thr Ala Ala Asp Ala Ala Arg Ala Phe Glu Leu Ala Glu Glu
35 40 45

Ile Ser Arg Asn Leu Lys Lys Ser Pro Ser Glu Phe Ile Asn Ser Trp
50 55 60

Pro Gly Ala Arg Ile Ser Thr Pro Asn Ser Glu Asn Glu Gly Met Tyr
65 70 75 80

Asn Val Ser Gly Gly Thr Leu Lys Leu Gly Asp His Leu Thr Ala Lys
85 90 95

Asp Ser Ser Ile Phe Ile Ser Ala Asp Lys Lys Lys Ile Glu Ser Val
100 105 110

Leu Leu Asn Leu Glu Gly Ser Cys Val Ser Arg Gln Asp Phe Lys Ile
115 120 125

Arg Tyr Pro Asn Tyr Leu Ile Ser Asn Ile Pro Arg Gly Gln Ser Ser
130 135 140

Ser Glu Thr Leu Thr Leu Ala Val Ile Lys Asn Gln Glu Lys Met Glu
145 150 155 160

Phe Ser Phe Pro Glu Thr Ser Pro Asp Cys Leu Ser Ala Ile Arg Ile
165 170 175

Ala Pro Ala Asp Ala Gln Met Leu Lys Ala Ala Glu Ala Phe Asn
180 185 190

<210> SEQ ID NO 4
<211> LENGTH: 516
<212> TYPE: DNA
<213> ORGANISM: Xanthomonas campestris

<400> SEQUENCE: 4
atgacaaact tccttaacag atcatcatat ccctacttta taataacact ccttgctgct 60
ttgattgcac cttcagcata tgcaactaaa atttcagcag cgacagcagc ggatgctgct 120
cgtgcgtttg aactagccga agaaatttcg agaaatctca aaaaatcacc ctctgaattt 180
attaattcat ggcctggagc cagaatttcg acgccaaatt cagaaaacga aggcatgtac 240
aacgtcagcg gaggaacatt aaaattaggt gatcacctaa ctgctaagga ctcttccatc 300
ttcatatcgg ccgataagaa aaagatcgag tcagtcctac tcaatctgga ggttcctgcg 360
tttctcgtca ggacttcaag asttcgatat ccgaattatc tgatttcaaa tattccgaga 420
ttttcgttcc cagaaacctc cccagattgc ctaagtgcca ttcgcatagc gccagcagac 480
gcacagatgc ttaaagctgc ggaagcattt aattaa 516

<210> SEQ ID NO 5
<211> LENGTH: 16
<212> TYPE: DNA
<213> ORGANISM: Xanthomonas campestris

<400> SEQUENCE: 5
taataacact ccttgc 16

-continued

```
<210> SEQ ID NO 6
<211> LENGTH: 25
<212> TYPE: DNA
<213> ORGANISM: Xanthomonas campestris

<400> SEQUENCE: 6
ctcggatccc tccatcttct cctga                                             25

<210> SEQ ID NO 7
<211> LENGTH: 27
<212> TYPE: DNA
<213> ORGANISM: Xanthomonas campestris

<400> SEQUENCE: 7
tgctctagac gccaaattca gaaaagc                                           27

<210> SEQ ID NO 8
<211> LENGTH: 27
<212> TYPE: DNA
<213> ORGANISM: Xanthomonas campestris

<400> SEQUENCE: 8
cccaagcttt taattaaatg cttccgc                                           27

<210> SEQ ID NO 9
<211> LENGTH: 15
<212> TYPE: DNA
<213> ORGANISM: Xanthomonas campestris

<400> SEQUENCE: 9
caacgtgttc cgtcc                                                        15

<210> SEQ ID NO 10
<211> LENGTH: 18
<212> TYPE: DNA
<213> ORGANISM: Xanthomonas campestris

<400> SEQUENCE: 10
gatcaacacc aattacgc                                                     18
```

ORFF AND ORFF' POLYPEPTIDES, NUCLEIC ACID MOLECULES ENCODING THE POLYPEPTIDES AND APPLICATIONS THEREOF

This application is a divisional application number 10/983,151 filed Nov. 5, 2004, now U.S. Pat. No. 7,186,562, which is a divisional of application number 10/232,459 filed on Aug. 30, 2002, now U.S. Pat. No. 6,887,980, which claims benefit of application number 60/316,546 filed on Aug. 31, 2001 and incorporates the same by reference.

FIELD OF THE INVENTION

The present invention relates to novel OrfF and OrfF' polypeptides, nucleic acid molecules encoding the polypeptides, and the applications thereof.

BACKGROUND OF THE INVENTION

Composting is the biological conversion of organic wastes, such as vegetable refuses, woodchips, leave litters or food wastes, into valuable products, such as fertilizers, substrates for growing mushroom, or biogas (methane) for use as energy sources. In comparison with chemical fertilizers, organic fertilizers are less expensive and have many agricultural advantages. For instances, soil modified with composts or organic fertilizers showed improvement of total porosity, increase of water stable aggregates (Nnabude, P. C., and Mbagwu, J. S., 2001, *Bioresour. Technol.*, 76:265-272) and accumulation of metals in soil (Guerrero, et al., 2001, *Bioresour. Technol.*, 76: 221-227; and Zinati, et al., 2001, *J. Environ. Sci. Health B*. 36: 229-243). Crop yield was enhanced and the growth period thereof was shortened (Ferrer, et al., 2001, *Bioresour. Technol.* 76: 39-44; Nnabude and Mbagwu, supra; and Guerrero, et al., supra). Termine, et al. found that leeks and turnips grown under organic fertilizations had less nitrate contents than those grown under inorganic fertilizations (Termine, et al., 1987, *Plants Foods Hum. Nutr.* 37:321-332).

Moreover, compost-modified soil could suppress occurrence of diseases on growing plants (Wuest, P. J., and Forer, L. B., 1975, *Mycopathologia* 55: 9-12; Kannangara, et al., 2000, *Can. J. Microbiol.* 46: 1021-1028). Therefore, the amounts of pesticides and fungicides used can be reduced or eliminated. In addition, since soil organisms can be killed by these pesticides and fungicides, it is considered that composts or organic fertilizers are environmentally safe and capable of retaining soil fertility. In fact, the soil modification with compost has been demonstrated as an effective method in remediation of contaminated soil (Vouillamoz, J., and Mike, M. W., 2001, *Water Sci. Technol.* 43: 291-295; Semple, et al., 2001, *Environ. Pollut.* 112: 269-283).

During composting, the active component mediating the biodegradation and conversion is the resident microbial community. As a composing process proceeds, the microbial community changes. For instance, some microbes were enriched and some were eliminated during the process (Peters, et al., 2000, *Appl. Environ. Microbiol.* 66: 930-936).

For many households or companies, plant leaves constitute the main portion of the starting materials for making organic fertilizers or composting. Crucifer plants are the most important vegetables worldwide, including *Brassica chinensis*, broccoli, cabbage, cauliflower, Brussels sprouts, Chinese cabbage, kale, radish, turnip and mustard. Leaves of the crucifers are either edible or discarded. *Xanthomonas campestris* pv. *campstris* is a bacterial pathogen of crucifer plants. It infects the leaves of the plants through natural openings (stomata and hydathodes) or wounds due to insect bites, resulting a black-rot disease of the plants (Williams, P. H., 1980, *Plant Dis.* 64: 736-742).

In addition, a compost-based biofilter for degradation of organic compounds have also been successfully developed (Lee, et al., 1999, *J. Air Waste Manag. Assoc.* 49: 1068-1074; Juteau, et al., 1999, *Appl. Microbiol. Biotechnol.* 52: 863-868). The biofilter is beneficial for the industry and the environment, such as bioremediation of hazardous waste sites, biofiltration of industrial water or air and forming a biobarrier to protect soil and ground water from contamination.

Our earlier studies showed that a spontaneous avirulent mutant of *X. campestris* pv. *campstris* strain 11(Xc11), which was called Xc11A, was likely resulted from transposition of a specific copy of insertion sequence IS1478a (Chen, et al., 1999, *J. Bacteriol.*, 181: 1220-1228) located in the genome of Xc11 to a position of 352 bp downstream (Hsiau, S. L., 1996, thesis, National Chung Hsing University). It is desired to isolate the black rot gene from Xc11 or the related strains and obtain a gene product useful in degradation of organic plant materials in a fast, efficient, simplified, controllable and environmentally safe manner.

SUMMARY OF THE INVENTION

In one aspect, the invention provides a novel OrfF polypeptide comprising an amino acid sequence of SEQ ID NO: 1 and the functional equivalents thereof, and a novel OrfF' polypeptide comprising an amino acid sequence of SEQ ID NO: 3 and the functional equivalents thereof. In one embodiment, the OrfF polypeptide is derived from *X. campestris* pv. *campstris* strain 11 (Xc11) and the OrfF' polypeptide is derived from *X. campestris* pv. *campstris* strain 17 (Xc17).

In another aspect, the invention provides an orfF nucleic acid molecule encoding the OrfF polypeptide of the invention, and the degenerate sequences thereof, and an orfF' nucleic acid molecule encoding the OrfF' polypeptide of the invention, and the degenerate sequences thereof. In one embodiment, the orfF nucleic acid molecule comprises a nucleotide sequence of SEQ ID NO: 2 and the orfF' nucleic acid molecule comprises a nucleotide sequence of SEQ ID NO: 4.

In another aspect, the invention provides a recombinant vector comprising the nucleic acid molecule of the invention and a regulatory sequence operatively linked thereof. In addition, the invention provides a recombinant cell or organism transformed with the nucleic acid molecule or the recombinant vector of the invention. Furthermore, the invention provides a method for preparing the polypeptide of the invention, comprising the steps of culturing the recombinant cell or organism of the invention under the conditions suitable for expressing the polypeptide, and recovering the polypeptide from the culture.

In still another aspect, the invention provides a method for detecting a black-rot disease of a crucifer plant, comprising the steps of providing a sample of a crucifer plant and treating the sample with the nucleic acid molecule of the invention as a probe under conditions such that the nucleic acid molecule can hybridize with a native orfF or orfF' nucleic acid molecule in the sample. The invention further provides a method for preventing the development of a black-rot disease of a crucifer plant, comprising the steps of providing an antisense nucleic acid fragment of the orfF or orfF' nucleic acid molecule of the invention and applying an effective amount of the antisense nucleic acid fragment to the crucifer plants.

In another aspect, the invention provides a method for preparing a recombinant crucifer plant resistant to a block-rot disease, comprising transforming a crucifer plant with an antisense nucleic acid fragment of the nucleic acid molecule of the invention. The invention further provides a recombinant crucifer plant resistant to a block-rot disease, which is prepared by the above method.

In another aspect, the invention provides an antibody directed to the polypeptide of the invention. The invention further provides a method for detecting a black-rot disease of a crucifer plant, comprising the steps of providing a sample of a crucifer plant and treating the sample with the antibody of the invention as a probe whereby the antibody reacts with a native OrfF or OrfF' polypeptide in the sample. The invention further provides a method for preventing the development of a black-rot disease of a crucifer plant, comprising the steps of applying an effective amount of the antibody of the invention to the crucifer plant.

In still another aspect, the invention provides a process for making organic fertilizers or composting, comprising the steps of providing an organic starting material, adding the OrfF or OrfF' polypeptide of the invention into the organic staring material to form a mixture, and incubating the mixture under conditions suitable for forming organic fertilizers or compost.

In still another aspect, the invention provides a biofilter for degradation or removal of organic compounds, comprising a filter support and the OrfF or OrfF' polypeptide of the invention or a recombinant cell or organism expressing the polypeptide distributed on the filter support.

Other aspects of the present invention will become apparent from the following descriptions.

BRIEF DESCRIPTION OF THE DRAWINGS

FIG. 1 The nucleic acid sequence of SEQ ID NO: 2 encoding the OrfF polypeptide of Xc11 and the amino acid sequence of SEQ ID NO: 1 deduced by the nucleic acid sequence of SEQ ID NO: 2. Amino acid residues are shown by single letter codes.

FIG. 11A and FIG. 11B The nucleic acid sequence of SEQ ID NO: 4 encoding the OrfF' protein of Xc17 and the amino acid sequence of SEQ ID NO: 3 deduced by the nucleic acid sequence of SEQ ID NO: 4. Amino acid residues are shown by single letter codes.

FIG. 12 Symptoms after injecting the cultural medium of Xc17 or the orfF::Km$^r$ knockout mutant of Xc11 into leaf veins of *Brassica chinensis*. (A) 6 days after injection with the cultural medium of the orfF::Km$^r$ knockout mutant of Xc11; (B) 6 days after injection with the cultural medium of Xc17; (C) 12 days after injection with the cultural medium of the orfF::Km$^r$ knockout mutant of Xc11; (D) 12 days after injection with the cultural medium of Xc17.

DETAILED DESCRIPTION OF THE INVENTION

Figure 2:
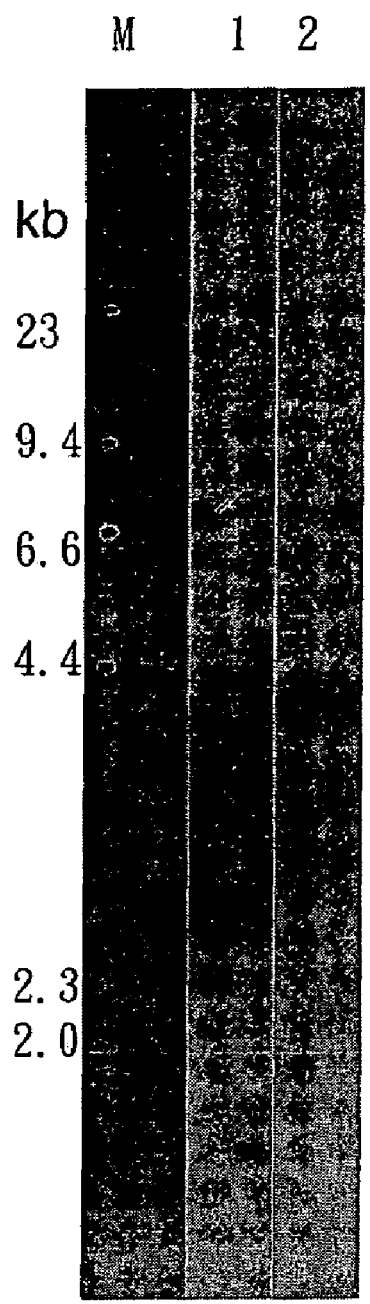
FIG. 2 Southern hybridization of BamHI-EcoRI restricted genomic DNAs of Xc11 and its orfF::Km.sup.r knockout mutant using a 0.35-kb orfF DNA fragment as probe. Lane 1, Xc11; lane 2, the orf::Km$^r$ knockout mutant; lane M, HindIII-restricted λ DNA fragments with sizes indicated on the left.

Due to concern about the potential for enrichment and possible transfer of pathogens into the food chain as well as to better control the compost quality, we have been looking for microbial proteins that have biodegradation capabilities with broad substrate spectrum. In the study, we successfully isolated novel genes from the genomic DNAs of Xc11 and Xc17, a closed-related virulent strain to Xc11, based on the above-mentioned 352-bp DNA fragment, and obtained polypeptides encoded by the genes capable of biodegradation of a plant body.

Accordingly, the invention provides an OrfF polypeptide comprising an amino acid sequence of SEQ ID NO: 1 and an OrfF' polypeptide comprising an amino acid sequence of SEQ ID NO: 3. In one embodiment of the invention, the OrfF polypeptide is prepared from Xc11 and the OrfF' polypeptide is prepared from Xc17. The polypeptide of the invention is capable of inducing a black-rot disease of a crucifer plant and has a biodegradation activity on plant materials.

The OrfF or OrfF' polypeptide of the invention comprises the functional equivalent of the same. In other words, the functional equivalent of the OrfF or OrfF' polypeptides of the invention are within the scope of the invention. As used herein, the "functional equivalent" of a polypeptide may contain one or more amino acid mutations (e.g., deletion, addition or substitutions) that result in silent changes on the corresponding amino acid codon and do not substantially affect the function of the polypeptide, such as the induction of a black-rot disease of a crucifer plant or the biodegradation activity on plant materials. For instance, the polypeptide of the invention comprising an amino acid D (aspartic acid) located in a certain position of the amino acid sequence is functionally equivalent to that comprising an amino acid E (glutamic acid) at the corresponding position since the two amino acids, D and E, are both classified as acid amino acids and have similar characteristics. More detailed technologies used to obtain the polypeptide of the invention and the functional equivalent thereof are described below.

In another aspect, the invention provides an orfF nucleic acid molecule encoding the OrfF polypeptide and the functional equivalents thereof, and an orfF' nucleic acid molecule encoding the OrfF' polypeptide and the functional equivalents thereof. In one preferred embodiment of the invention, the orfF nucleic acid molecule comprises a nucleotide sequence of SEQ ID NO: 2 and the orfF' nucleic acid molecule comprises a nucleotide sequence of SEQ ID NO: 4. The orfF nucleic acid molecule of the invention can be isolated from the Xc11 genomic DNAs and the orfF' nucleic acid molecule of the invention can be isolated from the Xc17 genomic DNAs. The nucleic acid sequences of the present invention can be engineered using methods generally known in the art in order to alter the OrfF or OrfF' encoding sequences for a variety, including but not limited to, alterations which modify the cloning, processing, and/or expression of the gene product.

The orfF or orfF' nucleic acid molecule of the invention comprises the degenerate sequences of the same. In other words, the degenerate sequences of the orfF or orfF' nucleic acid molecule are within the scope of the invention. "Degenerate sequences" of a nucleic acid molecule, as described herein, may contain one or more nucleotide mutations (e.g., deletion, addition or substitutions) that do not substantially affect the function of the nucleic acid molecule, such as encoding the polypeptide of the invention or hybridizing with a native orfF or orfF' gene in a plant sample. The term "a native orfF or orfF' gene in a plant sample" as used herein refers to a natural orfF or orfF' gene or the fragment thereof derived from a pathogenic bacterium, such as Xc11 or Xc17, contained in a sample of a plant. The term "a native OrfF or OrfF' polypeptide" as used herein refers to a natural OrfF or OrfF' polypeptide or the fragment thereof encoded by a native orfF or orfF' gene or the fragment thereof. More detailed technologies used to obtain the nucleic acid molecules of the invention and the functional equivalent thereof are described below.

In addition, the invention provides a recombinant vector comprising the nucleic acid molecule as set forth above and a regulatory sequence operatively linked thereto. The term "vector" used herein refers to a nucleic acid molecule capable of carrying and transferring a nucleic acid fragment of interest into a host cell for the purpose of expression or replication of the same. In particular, a vector refers to a plasmid, cosmid, bacteriophage or virus. Typically, the nucleic acid fragment of interest is operatively linked to a regulatory sequence such that, when introducing into a host cell, for instance, the nucleic acid fragment can be expressed in the host cell under the control of the regulatory sequence. The regulatory sequence may comprise, for example, a promoter sequence (e.g., cytomegalovirus (CMV) promoter, simian virus 40 (SV40) early promoter and T7 promoter), replication origin and other control sequences (e.g., Shine-Dalgano sequences and termination sequences). Preferably, the nucleic acid fragment of interest may be connected to another nucleic acid fragment such that a fused polypeptide (e.g., His-tag fused polypeptide) is produced and is beneficial to the subsequent purification procedures. The method for identifying and selecting the regulatory sequences is well known to persons skilled in the art and widely described in the literatures. The skilled persons can readily construct the recombinant vector of the invention according to the specification and the well-known literatures.

The recombinant vector or the nucleic acid molecule of the invention can be introduced into a host cell or an organism to produce a recombinant cell or organism for the expression of the polypeptide encoded by the nucleic acid molecule of the invention. A suitable host cell or organism can be derived from a plant, animal, bacterium (e.g., *E. coli*), fungus (e.g., yeast), insect, protozoa, virus, mycoplasma, etc. According to the conventional technologies in this art, persons skilled in the art can prepare a suitable recombinant vector and choose a suitable host cell or organism to express and isolate the polypeptide of the invention. Accordingly, the invention provides a method for preparing the polypeptide of the invention, comprising the steps of culturing the recombinant cell or organism as described above under the conditions suitable for expressing the polypeptide of the invention, and recovering the polypeptide of the invention from the culture. The polypeptide prepared by the method can be further purified by a conventional process (e.g., HPLC or a affinity column). Therefore, the recombinant cell or organism and the method for preparing the polypeptide are within the scope of the invention. Preferred embodiments of the host cell or organism and more detailed steps for conducting the method to obtain the polypeptide of the invention are described below.

The genetic engineering methods mentioned above such as DNA cloning, vector construction, transformation, protein expression, and purification can be accomplished by those skilled in this art, and which can be seen, for example, in *Molecular Cloning*: A Laboratory Manual, 2d ed., Cold Spring Harbor Laboratory Press, Sambrook, J., E. F. Fritsch and T. Maniatis eds. (1989).

According to the invention, the OrfF or OrfF' polypeptide is capable of inducing a black-rot disease of a crucifer plant, and the native orfF and orfF' genes encoding the OrfF and OrfF' polypeptides, respectively, derived from *X. campestris* pv. *campstris*, are considered as pathogenic genes for inducing the black-rot disease. Accordingly, the nucleic acid molecule of the invention can be used as a probe to detect a black-rot disease of a crucifer plant by a hybridization-based technology. The invention provides a method for detecting a black-rot disease of a crucifer plant, comprising the steps of providing a sample of a crucifer plant and treating the sample with the nucleic acid molecule of the invention as a probe under conditions such that the nucleic acid molecule can hybridize with a native orfF or orfF' gene in the sample. In one preferred embodiment, the sample is derived from leaves of the crucifer plant to be detected. Preferably, the crucifer plant is *Brassica chinensis*, broccoli, cabbage, cauliflower, Brussels sprouts, Chinese cabbage, kale, radish, turnip or mustard. The hybridization technology used in the method of the invention is well known in the art, such as Southern or Northern hybridization technologies as described by Sambrook et al., 1989, *Molecular Cloning*.

An antisense nucleic acid fragment is a single-stranded nucleic acid molecule (preferably less than 30 bases) having a sequence complementary to certain regions of a target gene and forming a hybrid duplex with the target gene by hydrogen-bonded base pairing. This hybridization can disrupt expression of both the mRNA and the protein encoded by the target gene. An antisense nucleic acid fragment is well known as a tool to inhibit the expression of a target gene (e.g., a pathogenic gene) and to enhance the resistance of a plant to pathogens. As mentioned above, Xc11 and Xc17 contain pathogenic genes orfF and orfF' of the black-rot disease in a crucifer plant. It is useful to provide an antisense nucleic acid fragment to inhibit the expression of the pathogenic orfF and orfF' genes and prevent the development of a black-rot disease of a crucifer plant. Accordingly, the invention provides a method for preventing the development of a black-rot disease of a crucifer plant, comprising the steps of providing an antisense nucleic acid fragment of the orfF or orfF' nucleic acid molecule of the invention and applying an effective amount of the antisense nucleic acid fragment to the crucifer plant. In one preferred embodiment, the antisense nucleic acid fragment is applied to leaves of the crucifer plant, preferably, *Brassica chinensis*, broccoli, cabbage, cauliflower, Brussels sprouts, Chinese cabbage, kale, radish, turnip or mustard. The synthesis of an antisense nucleic acid fragment of a target gene is well known in the art. Persons skilled in the art can synthesize a suitable antisense nucleic acid fragment of the orfF or orfF' nucleic acid molecule of the invention based on the disclosure of the specification in combination with the conventional technologies, such as those described in Sambrook et al., supra.

In addition, the antisense nucleic acid fragment of the orfF or orfF' nucleic acid molecule of the invention can be introduced into a crucifer plant to provide a resistance to a block-rot disease for the crucifer plant. Accordingly, the invention provides a method for preparing a recombinant crucifer plant resistant to a block-rot disease, comprising transforming a crucifer plant with an antisense nucleic acid fragment of the nucleic acid molecule of the invention. A recombinant crucifer plant resistant to a block-rot disease prepared by the above method is also within the scope of the invention. In one embodiment of the invention, the crucifer plant is *Brassica chinensis*, broccoli, cabbage, cauliflower, Brussels sprouts, Chinese cabbage, kale, radish, turnip or mustard. Preferably, the recombinant crucifer plant is resistant to a block-rot disease caused by Xc11 or Xc17.

In another aspect, the invention provides an antibody directed to the OrfF or OrfF' polypeptide of the invention. The polypeptide of the invention can be used as an immunogen to prepare an antibody directed to it. The OrfF or OrfF' polypeptide is purified as described above and introduced into a suitable animal, such as a rabbit or mouse, and the resultant antibody in the serum are collected, isolated and purified. The resultant antibody is a polyclonal antibody having a specific binding affinity to the OrfF or OrfF' polypeptide. Alternatively, the OrfF or OrfF' polypeptide can be used to prepare a monoclonal antibody against it by using a hybridoma technology well known in the art. In one preferred embodiment of the invention, a purified OrfF polypeptide is injected into a mouse in a suitable amount to generate an antibody against the OrfF polypeptide. The antibody can specifically bind to the OrfF polypeptide in an effective titer, such as 1:5000, preferably 1:10,000 and most preferably 1:20,000.

Due to the specificity, the antibody of the invention is useful in the detection of a black-rot disease of a crucifer plant. Accordingly, the invention provides a method for detecting a black-rot disease of a crucifer plant, comprising the steps of providing a sample of a crucifer plant and treating the sample with the antibody of the invention as a probe under conditions whereby the antibody reacts with a native orfF or orfF' polypeptide or the fragment thereof in the sample.

As described above, the OrfF or OrfF' polypeptide of the invention can induce a black-rot disease of a crucifer plant and is useful in biodegradation of an organic starting material (e.g., leaves of the crucifers) for making organic fertilizers or composting. Accordingly, the invention provides a process for making organic fertilizers or composting, comprising the steps of providing an organic starting material containing a plant body, adding the OrfF or OrfF' polypeptide of the invention into the organic starting material to form a mixture, and incubating the mixture under the conditions suitable for forming organic fertilizers or compost. In a preferred embodiment, the organic starting material may be vegetable refuses, wood-chips, leave litters or food wastes. The plant body contained therein is preferably derived from leaves of a crucifer plant, such as *Brassica chinensis*, broccoli, cabbage, cauliflower, Brussels sprouts, Chinese cabbage, kale, radish, turnip and mustard. The process for making compost, and materials, extracts, biochemicals or biogases thus produced as the end- or by-product through the process is within the scope of the invention. The OrfF and OrfF' polypeptides of the invention or the recombinant cell or organism expressing the OrfF and OrfF' polypeptides, and materials, extracts, biochemicals or biogases as described above can be used as integrants of feed, folder, medium, manure, compost, fertilizer or nutritional modifications or supplements for cultivation or feeding, killing, inactivation or restricting the growth of living organisms; as integrants of a soil conditioner or for biomediation of soil to improve the condition and fertility of the soil or modify a contaminated soil; and as integrants of fumigants or energy sources.

It is known that a biofilter in supporting specific microorganisms is capable of significantly degrading sulfur compounds and hydrocarbon vapors. Hydrogen sulfide, methyl mercaptan, and dimethyl disulfide have been successfully degraded using a biofiltration technique at the concentrations observed in wastewater treatment plant and paper-pulp mill fugitive emissions. Studies were also directed to the volatile organic compounds such as n-butane, benzene, and toluene. Benefits of using a biofiltration technology include economy of installation and operation, simplicity of maintenance, and ability to treat co-pollutants. Due to the biodegradation activity, the OrfF and OrfF' polypeptides of the invention or the recombinant cells or organisms expressing the OrfF and OrfF' polypeptides can be incorporated into a biofilter for degradation of organic compounds and is advantageous for the environmental safety. Accordingly, the invention provides a biofilter for degradation or removal of organic compounds, comprising a filter support and the OrfF and OrfF' polypeptides of the invention or a recombinant cell or organism expressing the OrfF and OrfF' polypeptides distributed on the filter support.

EXAMPLES

The present invention will become apparent with reference to the below examples. The examples described below are given by way of illustration only and not intended to be any limitation to the present invention.

Example 1

Genomic DNA of Xc11 was extracted from a 35 ml overnight culture and 200 g of genomic DNA was obtained. About 0.2 g of Xc11 genomic DNA was used as template to PCR-amplify the 352-bp DNA fragment with the primer pairs 352-L (5'-TAATAACACTCCTTGC-3') and Xc11A-R (5'-CTCGGATCCCTCCATCTTCTCCTGA-3'). The PCR fragment was gel-purified, radiolabelled with ($\alpha$-$^{32}$P)dCTP and used as a probe to screen about 4000 phage plaques from an Xc11 genomic library stock according to the method described by Sambrook et al., supra (Southern hybridization). Four positive bacteriophage clones were found. Of them, one clone was picked for further analysis. The phage DNA was prepared and restriction-mapped according to the method described by Sambrook et al., supra. A 2.6-kb EcoRI-BamHI DNA fragment of the phage DNA that included the 352-bp region was cloned into plasmid pUC18.

Example 2

The 2.6-kb EcoRI-BamHI DNA fragment was cloned into plasmid pUC18 (Yanish-Perron, et al., 1985, *Gene* 33: 103-119) and the nucleotide sequence was determined with universal forward and reverse primers. Within the sequence, only one orf (open reading frame) was found. Database search revealed that the orf did not show sequence homology with any known genes. It was named as orfF. FIG. 1 shows the nucleotide sequence of orfF and the deduced amino acid sequence of the putative OrfF polypeptide.

Example 3

A 1.3-kb BamHI Km$^r$ cassette from plasmid pUC4K (Amersham Pharmacia Biotech) was cloned into the SspI site of the orfF gene in the 2.6-kb EcoRI-BamHI DNA fragment and the resulting 3.9-kb EcoRI-BamHI fragment was cloned into suicide vector pSUP202 (Simon, et al., 1983, *Bio/technology* 2: 784-791). The recombinant plasmid was introduced to Xc11 via triparental mating (Ditta, et al., supra) and Km$^r$ transconjugants were selected. Genomic DNAs of the transconjugants were extracted, restricted with EcoRI and BamHI, and Southern hybridization was performed using PCR-amplified 0.35-kb orfF DNA fragment described in Example 1 as a probe. One transconjugant that had successful replacement of the chromosomal 2.6-kb orfF fragment with the 3.9-kb orfF::Km$^r$ fragment was picked (FIG. 2). The pathogenicity of this orfF::Km$^r$ knockout mutant was examined according to the method described by Daniel et al., 1984, *J. Gen. Microbiol.* 130: 2447-2455, and the results showed that the knockout mutant did not elicit any rotting symptom with any of the 8 test turnip seedlings. It was concluded that the orfF gene was responsible for the rotting capability of Xc11.

Example 4

Figure 3:
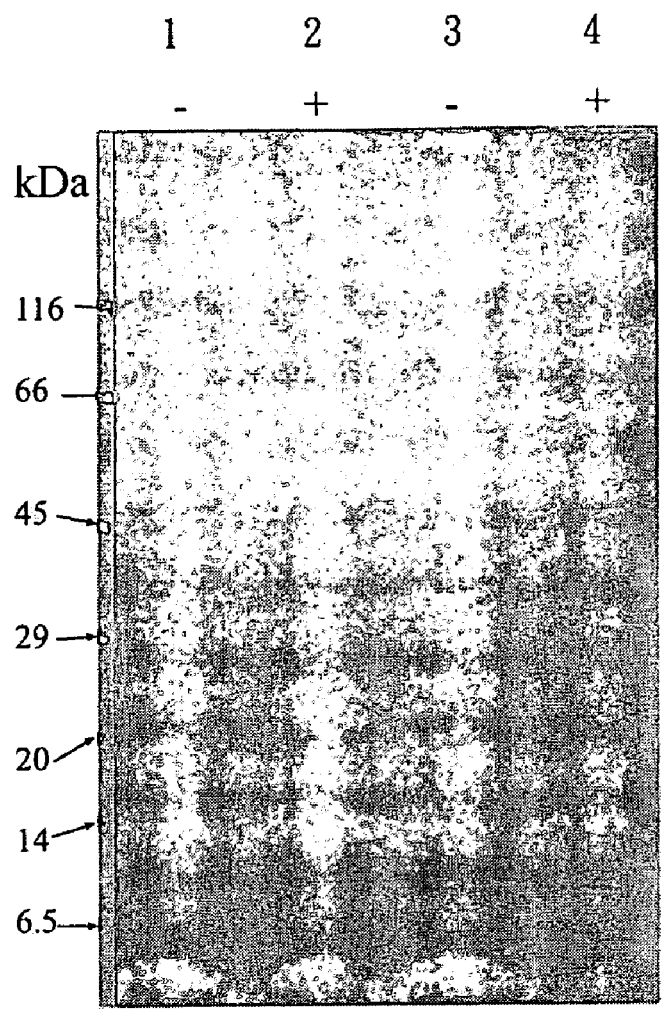
FIG. 3 Autoradiograph of $^{35}$S-labelled cellular proteins of plasmid-containing BL21(DE3) pLysS cells separated by SDS-PAGE. Lanes 1 and 2, pET21b::orfF-containing BL21 (DE3) pLysS cells; lanes 3 and 4, pET21b-containing BL21 (DE3) pLysS cells; Lanes 1 and 3, without IPTG induction; lanes 2 and 4, with IPTG induction. Sizes of maker proteins are indicated on the left.

The orfF gene DNA fragment was PCR-amplified with plasmid pTc$\alpha$. and primer pairs L (5'-TGCTCTAGACGC-CAAATTCAGAAAAGC-3') and R1 (5'CCCAAGCTTT-TAATTAAATGCTTCCGC-3'), and gel-purified. The orfF DNA fragment was cloned into the XbaI and HindIII sites of plasmid pET21b (Novagen) and transformed into *E. coli* BL21(DE3) pLysS (Novagen). Expression of the orfF gene in the transformant was examined according to the method modified from the methods of Tabor and Richardson, 1985, *Proc. Natl. Acad. Sci. USA*. 82: 1074-1078 and Ajdic and Ferretti, 1998, *J. Bacteriol.* 180: 5727-5732. Basically, 1 mM IPTG was added into 5 ml of mid-log phase culture and incubation was continued for 1.6 hour, which was followed by $^{35}$S-Methionine labeling for 10 minutes. The cells were harvested by centrifugation and dissolved in 100 µl of SDS gel-loading buffer, of which 15 µl was used for SDS-PAGE analysis and autoradiography. As shown in FIG. 3, the orfF gene was expressed as a 13 kd protein with the culture of the pET21b::orfF-containing cells, but not with the culture of the pET21b-containing cells. Therefore, the orfF gene could be expressed as a 13 kd OrfF protein in vivo by the T7 promoter in pET21b.

Example 5

Figure 4:
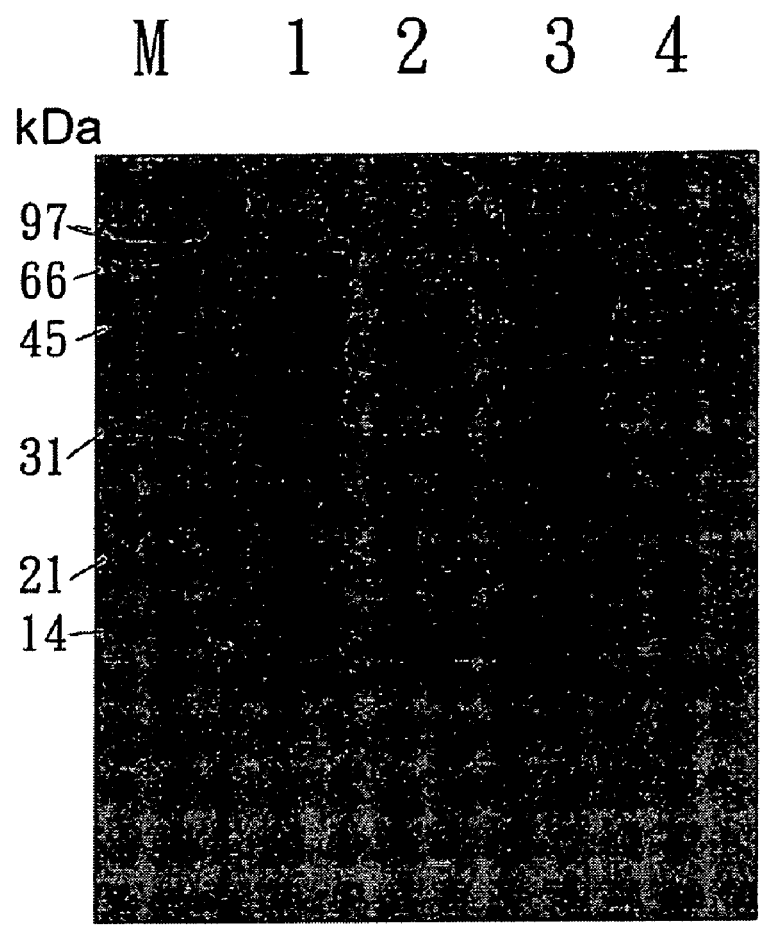
FIG. 4 SDS-PAGE and Coomasie blue staining of cellular proteins of plasmid-containing DH1(DE3) cells. Lanes 1 and 2, pET21b::orfF-(His)6-containing DH1(DE3) cells; lanes 3 and 4, pET21b-containing DH1(DE3) cells; lane M, protein size markers with sizes indicated on the left. Lanes 1 and 3, without IPTG induction; lanes 2 and 4, with IPTG induction.

For the purpose of generating an OrfF-(His)6 fusion protein and an antibody against the protein, the orfF gene DNA fragment was PCR-amplified and cloned into the NdeI and HindIII sites of plasmid pET21b (Novagen) so that a Shine-Dalgano sequence was located in front of the orfF gene and a (His)6-tag sequence was linked to the C-terminal end of the expressed OrfF protein, and the plasmid was transformed into DH1(DE3) (laboratory stock). For induction of the OrfF-(His)6 protein, 1 mM IPTG was added to the mid-log phase culture of the transformant and incubation was continued for 2 hours. Cell pellets were harvested and the total cellular proteins were analyzed by SDS-PAGE. As shown in FIG. 4, the cells harboring pET21b::OrfF-(His)6 showed an overexpression of a protein with the same size as expected for the OrfF-(His)6 protein (14 kd) after IPTG induction. On the other hand, cells harboring pET21b did not show induction of proteins of similar sizes.

Example 6

Figure 5:
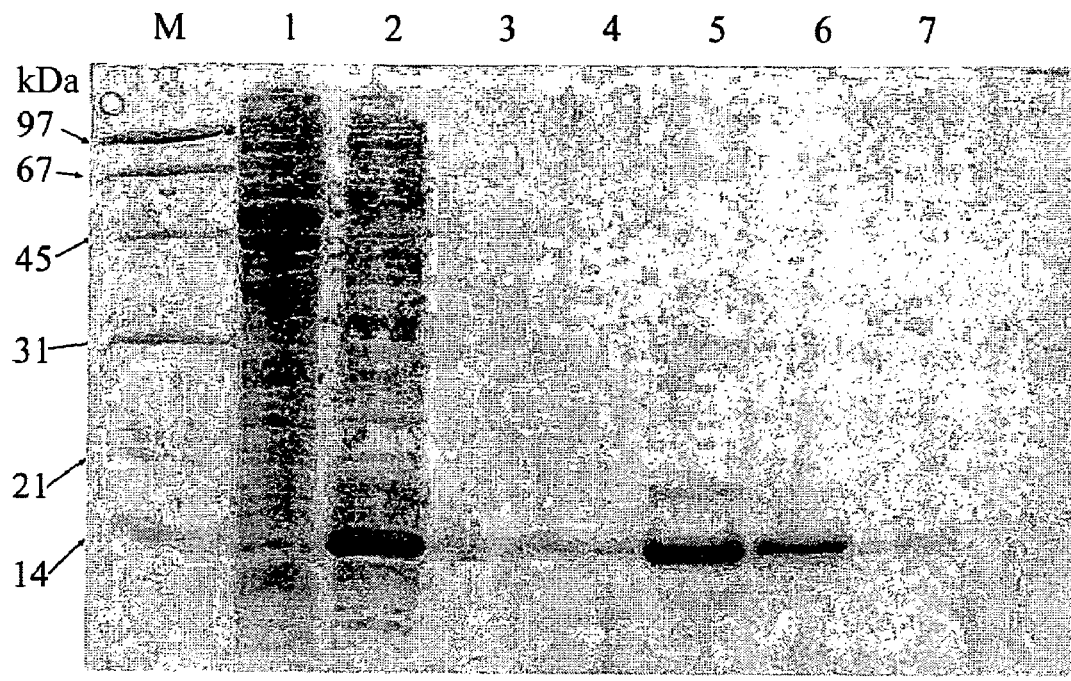
FIG. 5 SDS-PAGE and Coomasie blue staining of proteins in flow-through and the first three eluents during purification of the OrfF-(His)6 protein by affinity chromatography. Lane 1, total cellular proteins from uninduced cells; lane 2, total cellular proteins from IPTG-induced cells; lane 3 and 4, flow-throughs; lane 5, 6 and 7, the first three eluents; lane M, protein size markers with sizes indicated on the left.
Figure 6:
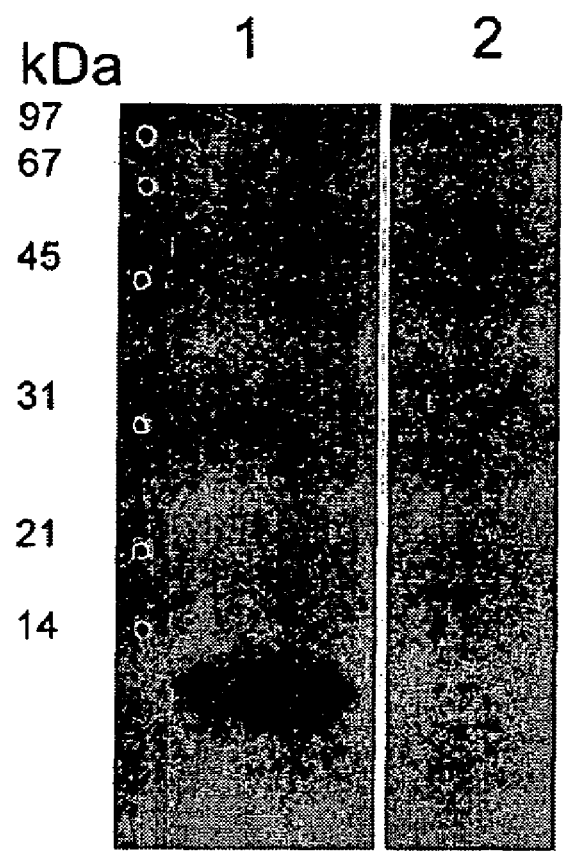
FIG. 6 Western hybridization of the total cellular proteins in IPTG-induced culture of the pET21b::orfF-(His)6-containing DH1(DE3) cells (lane 1) and the proteins in the eluent during purification of the OrfF-(His)6 protein by affinity chromatography (lane 2), using anti-His antibody as probe.

Purification of the OrfF-(His)6 protein from culture of pET21b::orfF-(His)6-containing cells was performed according to the methods described in the pET System manual (Novagen, 9$^{th}$ edition). Basically, 1 mM IPTG was added to 50 ml of the mid-log phase culture of the pET21b::OrfF-(His)6-containing DH1(DE3) cells and incubation was continued for 2 hours. Cell pellets were harvested and cell extract was prepared by sonication. Inclusion body in the cell extract was collected through several centrifugation and washing steps and about 100 mg of inclusion body was obtained. The OrfF-(His)6 protein in the inclusion body was purified by the method modified from the method of Shi et al., 1997, *Biotechniques* 23: 1036-1038. The pellet was first dissolved in 2 ml of the binding buffer (20 mM Tris, 0.5 M NaCl, 5 mM imidazol, and 8 M urea; pH 7.8) completely and 2 ml of Ni-NTA agarose (Qiagen) was added. After incubation overnight at 4° C., the mixture was packed in an empty column and washed with 5 volumes (10 ml) of the binding buffer first and later 5 volumes (10 ml) of the wash buffer (20 mM Tris, 0.5 M NaCl, 20 mM imidazol, and 8 M urea; pH 7.8). Flow-through from the wash buffer was collected. Three volumes (6 ml) of the elution buffer (20 mM Tris, 0.5 M NaCl, 0.3 M imidazol, pH 7.8) was then applied and the eluent was collected into a tube every 1 ml. As a result, 6 tubes of eluent were collected. For the first 3 tubes containing the eluent from the elution buffer and the 2 tubes containing the flow-through from the wash buffer, 15 µl each was taken for SDS-PAGE analysis. As shown in FIG. 5, a protein band of 14 kd was observed with the 5 samples examined. Solutions in the 6 tubes containing the eluent from the elution buffer were pooled and 5 .mu.l was used for SDS-PAGE analysis and probing with anti-His antibody (Invitrogen) (Western hybridization). Total cellular proteins from IPTG-induced culture of the pET21b::orfF-(His)6-containing cells was analyzed together as control. As shown in FIG. 6, a hybridization signal corresponding to a protein of 14 kd was observed with the eluent and the total cellular proteins of the IPTG-induced culture. Thus, the eluent contained only one 14-kd protein with a (His)6 tag in the sequence. The purified protein was likely the OrfF-(His)6 protein.

Example 7

Figure 7:
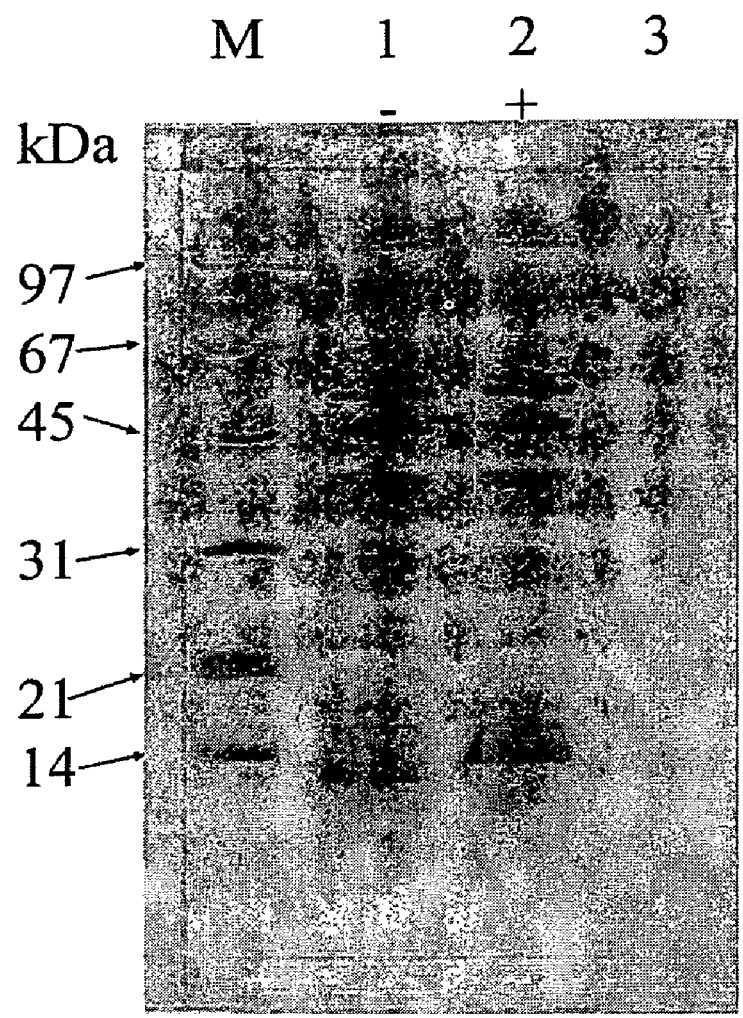
FIG. 7 SDS-PAGE and Coomasie blue staining of the HPLC-purified protein from culture of the pET21b::orfF-(His)6-containg DH1(DE3) cells. Lane 1, total cellular proteins from uninduced cells; lane 2, total cellular proteins from IPTG-induced cells; lane 3, proteins in eluent of the HPLC protein peak. Lane M, protein size markers with sizes indicated on the left.

To confirm that the protein purified in Example 6 was indeed the OrfF-(His)6 protein, the protein in the eluent in Example 6 was further purified by HPLC (High Performance Liquid Chromatography) and subjected to N-terminal sequencing. The total of approximate 6 ml of eluent in Example 6 was loaded onto a C18 column (5C-18-Ms, Cosmosil) and eluted with an acetonitrile gradient (0% to 60% acetonitrile in 1% trifluoroacetate). A protein peak was observed and the protein was collected as a 2 ml solution. The solution was concentrated into 50 .mu.l by Centricon 10 (Millipore) and 10 .mu.l were analyzed by SDS-PAGE. Total cellular proteins of both IPTG-induced and uninduced cultures of pET21b::orfF-(His)6-carrying DH1(DE3) cells were analyzed together for comparison. As shown in FIG. 7, a single protein band corresponding to the 14-kd OrfF-(His)6 protein was observed with the HPLC-purified protein sample and the total cellular proteins of the IPTG-induced culture. The remaining 40 μl HPLC-purified protein solution was subjected to N-terminal sequencing. The result indicated that the first 5 amino acid residues of the purified protein are the same as those expected from the OrfF protein sequence (FIG. 1). This result and the result from Example 6 clearly indicated that protein purified by the procedures in Example 6 was indeed the OrfF-(His)6 protein.

Example 8

Figure 8:
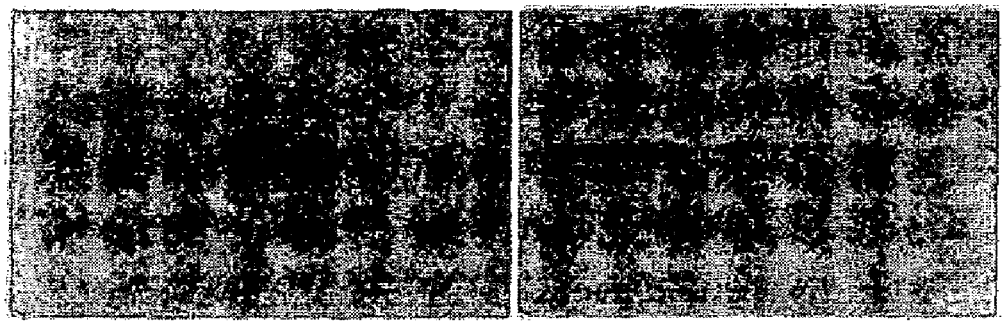
FIG. 8 Western hybridization of total proteins and cultural medium proteins from cultures of Xc17, Xc11 and the or TF::Km$^r$ knockout mutant of Xc11 using antibody against OrfF-(His)6 protein as a probe. Lanes 1-3, total proteins from the culture of Xc17 (lane 1), Xc11 (lane 2) and the orfF::Km$^r$ knockout mutant of Xc11 (lane 3); lanes 4-6, cultural medium proteins from the culture of Xc17 (lane 4), Xc11 (lane 5) and the orfF::Km$^r$ knockout mutant of Xc11 (lane 6).

The OrfF-(His)6 protein prepared according to the procedures in Example 4 was quantitated by the protein assay kit (Bio-rad). About 5 μg of the protein was used to immunize a mouse in order for generation of antibody against the OrfF-(His)6 protein. The antibody was used as 1:20000 dilution for probing the cell extracts from both IPTG-induced and uninduced cultures of pET21::orfF-(His)6-carrying DH1(DE3) cells, and a hybridization signal corresponding to the OrfF-(His)6 protein was observed. 250 ml of the cultures of Xc11, Xc17, a virulent strain closely related to Xc11, and the orfF::Km$^r$ knockout mutant of Xc11 were grown in secretion medium (Rossier, et al., 1999, *Proc. Natl. Acad. Sci. USA*. 96: 9368-9373) and were checked for production and secretion of the OrfF protein according to the method described by Rossier, et al., 1999, supra. To prepare the total protein fractions, proteins of the 5 ml cultures of the both cells were TCA-precipitated, and dissolved in 100 μl SDS gel-loading buffer. To prepare the culture medium protein fractions, the remaining 200 ml cultures of both cells were centrifugated and the cell-free supernatants were filtered through a 0.22 μm filter (GPWP04700, Millipore). The proteins in the filtrates were TCA-precipitated and dissolved into 500 .mu.l SDS gel-loading buffer. Fifteen μl of total protein fractions and culture medium protein fractions of the three cells were used for SDS-PAGE analysis, followed by probing with anti-OrfF-(His)6 antibody (Western hybridization). As shown in FIG. 8, hybridization signals were observed with both the cultural medium proteins and the total proteins from culture of Xc11 and another virulent strain Xc17, but not with those from culture of the orfF::Km$^r$ knockout mutant of Xc11. However, the hybridization signals correspond to a protein of 21 kd in size, instead of 13 kd which is the size of OrfF protein in Xc11 as detected in Example 4.

Example 9

Figure 9:
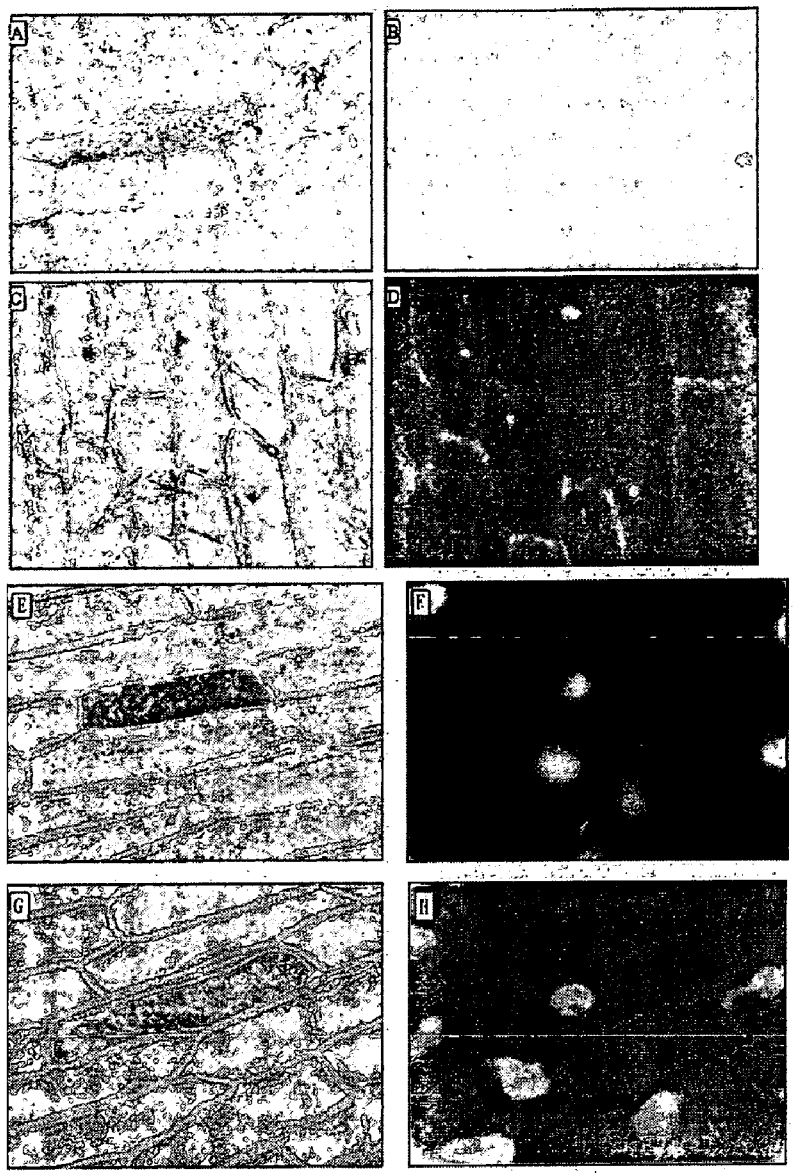
FIG. 9 Gus and DAPI stains of onion epidermal cells bombarded with pBI221 and its derivatives. A and B, pBI221; C and D, BI221 containing orfF; E and F, pBI221 containing orfF with deletion of the nucleotides encoding the three consecutive lysine residues in the OrfF-GUS protein; G and H, pBI221 containing orfF with mutation of the nucleotides encoding the three consecutive lysine residues in the OrfF-GUS protein. A, C, E and G, Gus stains; B, D, F and H, DAPI stains.

The orfF gene DNA fragment was PCR-amplified and cloned into the XbaI and SmaI sites of plant expression plasmid pBI221 (Clontech), in which expression of the OrfF-GUS fusion protein was under the control of CaMV 35S promoter. The recombinant plasmid was introduced into onion epidermal cells via particle bombardment according to the method described by Varagona et al., 1992, *Plant Cell* 3: 105-113. Gus staining was then performed according to the method described by Varagona et al., 1992, supra and the cells were observed under a light microscope. It was found that blue stains were localized in the nucleus of the cells bombarded with the orfF gene-carrying pBI221 plasmid. In contrast, blue stains were observed in the cytoplasm of cells bombarded with pBI221 (FIG. 9). The cells were then stained with a nucleic acid stain, DAPI, and observed under fluorescence microscope (Varagona, et al., 1992). The light blue fluorescence stains co-localized with the Gus stains in cells bombarded with the orfF gene-carrying pBI221 plasmid, but not with those in cells bombarded with pBI221 (FIG. 9). This indicated that the OrfF-GUS protein was capable of entering nuclei of the plant cells, whereas the GUS protein could stay in the cytoplasm of the plant cells. Site-directed mutagenesis was performed with the orfF gene-carrying pBI221 plasmid so that the three lysine residues at $28^{th}$ 29th and $30^{th}$ residues in the OrfF sequence were either deleted or changed into three threonine residues. The resulting two mutant plasmids were again bombarded into onion cells followed by Gus and DAPI stains. The results showed that the Gus stains were observed in the cytoplasm of the onion cells with the two mutant plasmids (FIG. 9). It was thus concluded that OrfF protein, when introduced into plant cells, could enter plant nucleus.

Example 10

Figure 10:
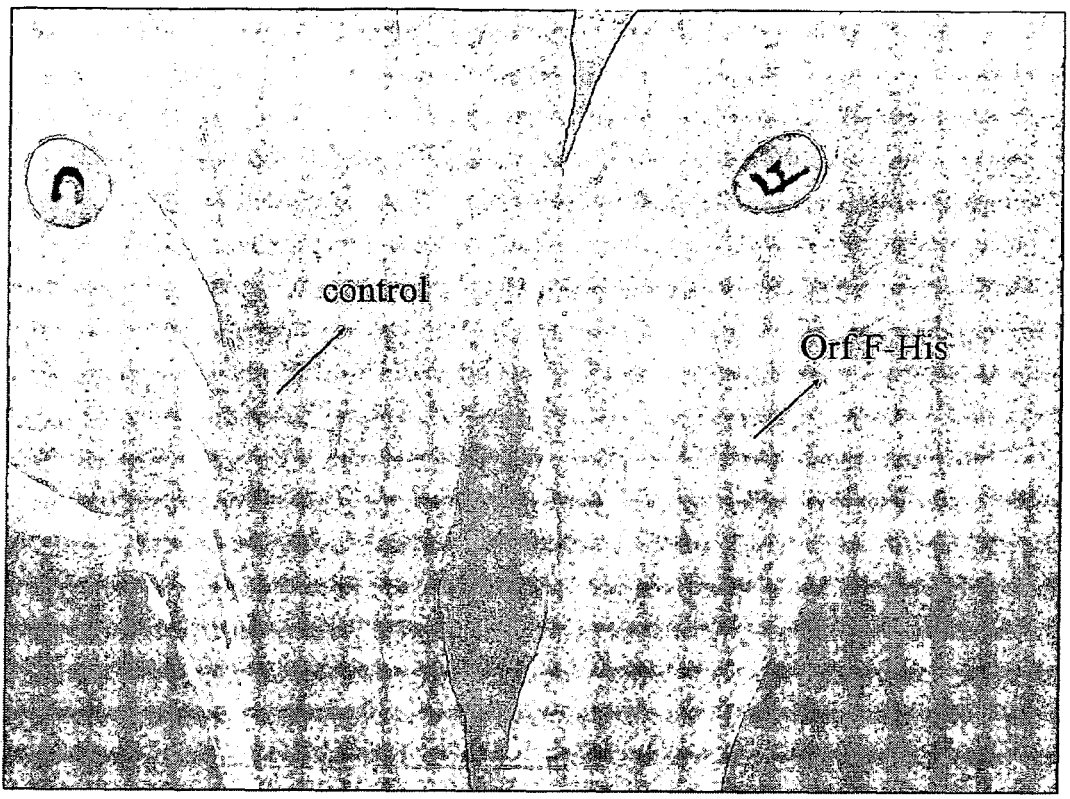
FIG. 10 The black-rot symptom in a leaf vein of *Brassica chinensis* after inoculation with buffer containing the OrfF-(His)6 protein. The buffer without the OrfF-(His)6 protein served as control. Sites of inoculation are indicated by arrows.

The OrfF-(His)6 protein was purified according to the method described in example 6, except that the last elution step was replaced by the following renaturation and elution steps. After washing with five volumes of wash buffer as described in Example 6, the column was washed 9 times each with 10 ml of binding buffers containing either 8 M, 7 M, 6 M, 5 M, 4 M, 3 M, 2 M and 1 M urea in order and, lastly, 10 ml of biding buffer without urea. Three volumes (6 ml) of elution buffer were applied and about 5 ml of eluent was collected. Protein concentration in the eluent was determined by protein assay kit (Bio-rad), which was 700 ng per .mu.l. A test shown in FIG. 10, black-rot symptom was observed in the injection site with the OrfF-(His)6 protein-containing elution buffer, but not with the elution buffer only. Therefore, OrfF-(His)6 protein alone was capable of rotting leaves of *Brassica chinensis*.

Example 11

Primer pairs pLXC11F4 (5'-CAACGTGTTCCGTCC-3') and PTCaL2 (5'-GATCAACACCAATTACGC-3') corresponding to the sequences upstream of IS1478a and downstream of orfF in Xc11 were used to amplify the corresponding region in Xc17. A 2.5-kb DNA fragment was obtained, cloned and sequenced. The 2.5-kb sequence was found to be identical to the expected 4.0 kb sequence in the corresponding DNA region of Xc11, except that the IS1478a copy located upstream of orfF in Xc11 and its adjacent 5-bp sequence were deleted in Xc17. The deletion resulted in generation of a new open reading frame by in-frame addition of 246-bp sequence 5' to orfF. This new orf is called orfF'. The OrfF' protein not only can be generated and secreted in Xc17 but also in Xc11, which should be due to spontaneous excision of the IS1478a copy and the adjacent 5-bp sequence in Xc11. The OrfF protein could not be generated in the orfF::Km$^r$ knockout mutant of Xc11. FIGS. 11A and B show the nucleotide sequence of orfF' and the deduced amino acid sequence of the putative ORfF' protein.

Example 12

One-hundred-and-twenty ml of cultures of Xc17 and the orfF::Km$^r$ knockout mutant of Xc11 were grown in secretion medium (Rossier, et al., 1999, *Proc. Natl. Acad. Sci. USA*. 96: 9368-9373) and concentrated by Centricon (Millipore). Protein concentrations were determined by protein assay kit (Bio-rad) wherein 19.32 .μg per ml for Xc17 and 20.59 .mu.g per ml for the knockout mutant. Fifty μl of each was applied to leaf veins of *Brassica chinensis* through a 1-ml syringe. As shown in FIG. 12, black-rot symptom was observed in the injection site with the cultural medium of Xc17, but not with that of the knockout mutant. Therefore, the OrfF' protein in the cultural medium of Xc17 was capable of rotting leaves of *Brassica chinensis*.

What is claimed is:

1. A fused polypeptide comprising an OrfF polypeptide comprising an amino acid sequence of SEQ ID NO: 1 fused to a polypeptide tag that can assist in purification of the OrfF polypeptide.

2. A fused polypeptide of claim 1, wherein the polypeptide tag is a histidine tag.

3. A fused polypeptide comprising an OrfF' polypeptide comprising an amino acid sequence of SEQ ID NO: 3 fused to a polypeptide tag that can assist in purification of the OrfF' polypeptide.

4. The fused polypeptide of claim 3, wherein the polypeptide tag is a histidine tag.

* * * * *